United States Patent [19]
Al-Tameem

[11] Patent Number: 5,643,305
[45] Date of Patent: Jul. 1, 1997

[54] DEVICE FOR EXCISION OF A FISTULA

[76] Inventor: Moshin Al-Tameem, King Saud University and King Khalid University Hospital, P.O. Box 7805, Riyhadh, Saudi Arabia, 11472

[21] Appl. No.: 341,187

[22] Filed: Nov. 18, 1994

[51] Int. Cl.$^6$ ............................................. A61B 17/32
[52] U.S. Cl. .................... 606/180; 606/170; 606/184; 128/754
[58] Field of Search ...................... 606/184, 167, 606/170, 171, 180; 128/753, 754, 751

[56] References Cited

U.S. PATENT DOCUMENTS

| | | |
|---|---|---|
| 2,447,169 | 8/1948 | De Sousa . |
| 3,552,626 | 1/1971 | Astafiev et al. .......................... 227/19 |
| 3,776,237 | 12/1973 | Hill et al. . |
| 3,970,089 | 7/1976 | Saice ........................................ 604/256 |
| 4,476,863 | 10/1984 | Kanshin et al. ........................ 606/153 |
| 5,112,345 | 5/1992 | Farr ........................................... 606/180 |
| 5,133,727 | 7/1992 | Bales et al. .............................. 606/170 |
| 5,193,526 | 3/1993 | Daikuzono . |
| 5,318,528 | 6/1994 | Heaven et al. ...................... 606/205 X |
| 5,334,206 | 8/1994 | Daikuzono ................................ 606/7 |
| 5,488,958 | 2/1996 | Topel et al. ............................. 606/180 |

FOREIGN PATENT DOCUMENTS

| | | | |
|---|---|---|---|
| 441974 | 8/1991 | European Pat. Off. . | |
| 601709 | 6/1994 | European Pat. Off. . | |
| 2821955 | 11/1979 | Germany ............................. 128/751 |
| WO88/10098 | 12/1988 | WIPO . | |

OTHER PUBLICATIONS

Soviet Patent Abstracts, Sect. PQ, Week 8911 29 Apr. 1989, Derwent Publications Ltd., London, GB; Class P31, AN 89-083251, Soft tissue . . . , & SU-A-1 421 319 (Kiev Med Inst), 7 Sep. 1988, abstract.

*Primary Examiner*—Michael Buiz
*Assistant Examiner*—Patrick W. Rasche
*Attorney, Agent, or Firm*—Cushman Darby & Cushman Intellectual Property Group of Pillsbury Madison & Sutro, LLP

[57] ABSTRACT

The device includes a bar having a longitudinal axis and adapted to be inserted into a fistulous tract. A cutting tool cooperates with the bar such that the cutting tool separates the fistulous tract from the surrounding tissue by coring the fistula.

9 Claims, 9 Drawing Sheets

5,643,305

DEVICE FOR EXCISION OF A FISTULA

BACKGROUND OF THE INVENTION

1. Field of the Invention

The present invention pertains to a surgical instrument for removing a fistula, and in particular, to a surgical instrument including a thin bar that is inserted into a fistulous tract and a cutting tool cooperating with the bar for coring the fistulous tract from the surrounding tissue.

2. Brief Description of the Art

The conventional technique for removing a peri-anal fistula, for example, requires making a deep incision from the edge of the anus in the plane of the fistula until the incision reaches the fistula. The fistula is then excised from the surrounding tissue and removed from the patient.

However, such an incision cuts the lower fibers of the anal sphincter that traverse the course of the incision. Therefore, this operation is likely to impair the patients stool or flatus continence, especially if the fistula is located a relatively large distance from the anus or is recurrent. Such an operation also leaves a large cavity which usually takes many weeks to heal. During the long healing period, the patient suffers pain, requires frequent dressings, and is likely to be absent from work. This can result in a significant economic loss for the patient. Furthermore, in a high peri-anal fistula, where the fistula is located a relatively large distance from the anus, the above-described operation can not be used because incontinence would be inevitable from the relatively large incision that would be required.

Removing a high peri-anal fistula requires diverting the faeces to a defunctioning colostomy, then surgically removing the fistula using the procedure discussed above. A few months later the colostomy is closed. It can be easily appreciated that this treatment for a high perianal fistula entails a great deal of suffering and risk for the patient and has a high cost.

SUMMARY OF THE INVENTION

It is an object of the present invention to provide a device for removing a fistula that overcomes the problems associated with the previous method for removing a fistula. In this regard, it is a further object to minimize the size of the cavity created by the removal of the fistula and, thus, reduce the healing time and the trauma to the patient's anal tissue and sphincteric muscle. By avoiding cutting a relatively large portion of the anal tissue and sphincteric muscle the risk of incontinence is reduced.

In accordance with the principles of the present invention, the foregoing objects are achieved by providing a device for excising a fistula, which includes a fistulous tract, by coring the fistula from the surrounding tissue. The device includes a bar that is adapted to be inserted into the fistulous tract and a cutting tool that cooperates with the bar. In one embodiment of the present invention, for example, the cutting tool moves relative to the bar in a direction generally parallel to the longitudinal axis of the bar, using the bar as a supporting member, for excising the fistula from the patient by coring the fistulous tract from the surrounding tissue. In another embodiment of the present invention, the bar and cutting tool are coupled to one another such that the cutting does not move longitudinally relative to the bar. The fistulous tract is cored from the surrounding tissue by rotating the entire device or by rotating only the cutting tool.

It is another object of the present invention to provide a method for using the above-identified device for removing a fistula. This method includes inserting the bar into a first end of a fistulous tract. In one embodiment the cutting tool is moved in a direction generally parallel to the longitudinal axis of the bar such that the cutting tool cuts the tissue surrounding the fistulous tract therefrom. In another embodiment the entire device is rotated about the fistulous tract to separate the fistulous tract from the surrounding tissue.

Further objects, features, and characteristics of the present invention, as well as the functions of the related elements of structure, and the economies of manufacture, will become more apparent upon consideration of the foregoing description and the appended claims with reference to the accompanying drawings, all of which form a part of the specification, wherein like a reference numerals designate corresponding parts of the various figures.

DETAILED DESCRIPTION OF THE PRESENTLY PREFERRED EXEMPLARY EMBODIMENTS

Figure 1:
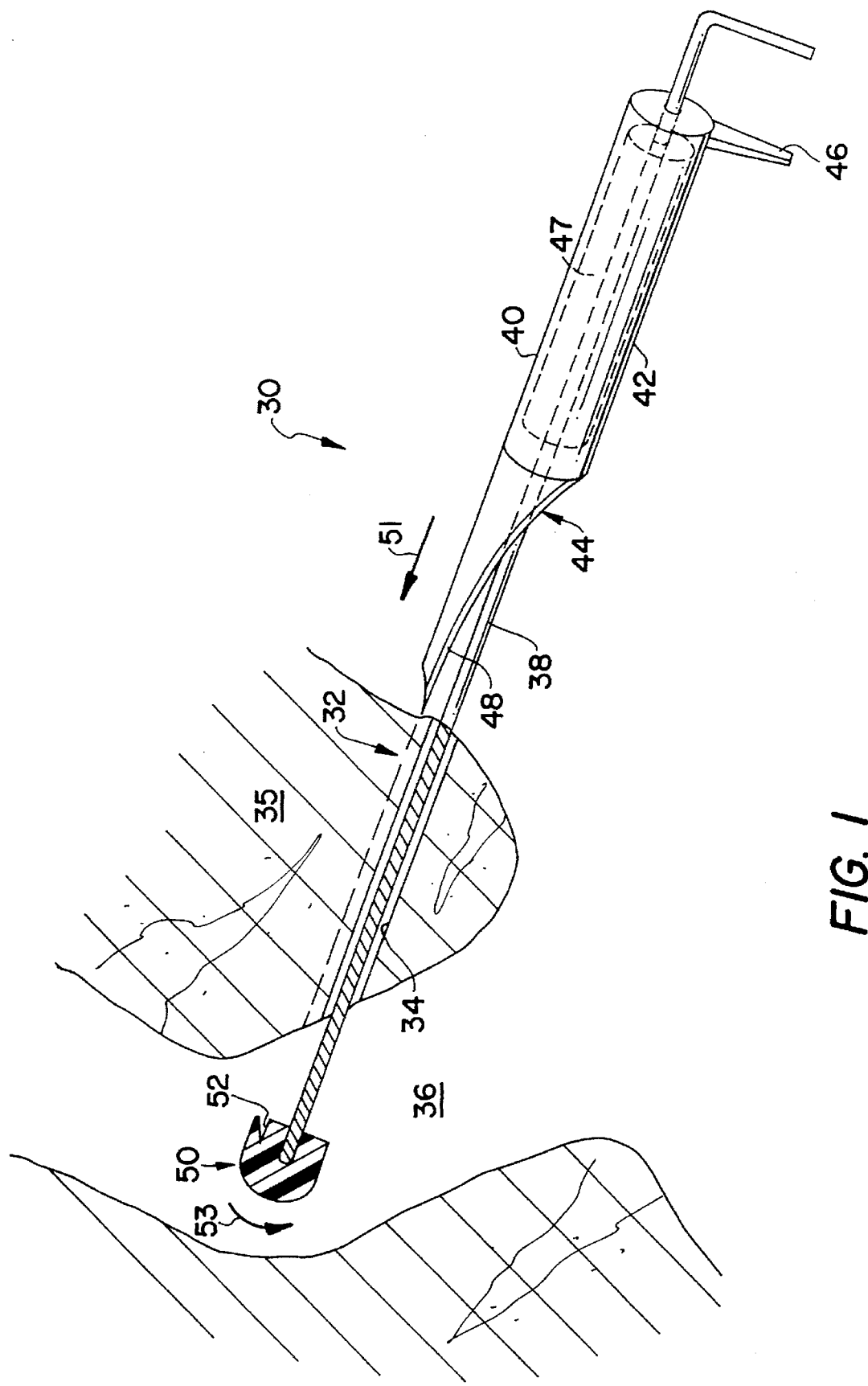
FIG. 1 is a side view, partially in section, of a first embodiment of a device and method for excising a fistula according to the principles of the present invention.

FIG. 1 illustrates a device, generally indicated at 30, for removing a fistula 32 from a patient according to the present invention. In the illustrated embodiment, fistula 32 is a peri-anal fistula including a fistulous tract 34 extending from anal canal 36 to an exterior portion of the patient near the rectum. Device 30 includes a thin stiff bar 38, which is similar to a probe, adapted to be inserted into fistulous tract 34. A cutting tool 40 operates in conjunction with bar 38 such that bar 38 forms a base or support member for cutting tool 40, enabling cutting tool 40 to slide in a direction corresponding to the longitudinal axis of bar 38 as well as rotate about bar 38.

Cutting tool 40 includes a body portion 42 and a selectively detachable cutting blade 44 attached to body portion 42. Because cutting blade 44 is selectively detachable from body portion 42, other cutting blades can be used in conjunction with body portion 42. In the illustrated embodiment, body portion 42 is cylindrical, has a thin wall, and surrounds a portion of bar 38. A handle 46 is attached to a proximal end of body portion 42 and cutting blade 44 is attached to a distal end thereof.

A cylindrical-shaped stabilizer 47 is fixed to a part of bar 38 with remains outside the patient's body. Body portion 42 of cutting tool 40 moves with respect to stabilizer 47. Stabilizer 47 ensures that cutting blade 44 is spaced apart from bar 38 so that cutting tool 40, in conjunction with bar 38, cores out the fistulous tract 34 by cutting the tissue around the circumference of the fistula, thereby detaching fistula 32, including fistulous tract 34, from the surrounding tissue. Because body portion has a thin wall, the excised portions of fistulous tract 34 can enter body portion 42 during the removal procedure.

Cutting blade 44 can have a wide variety of shapes and sizes. For example, it may take the shape of an arc or may take the shape of a pen refill, as illustrated in FIG. 1. In the illustrated embodiment, a cutting edge 48, which extends generally from the distal end of body portion 42 to the distal end of cutting blade 44 acts as the cutting surface of cutting blade 44 after the cutting blade has been inserted through tissue 35, as indicated by the dashed line in FIG. 1.

A cap 50 is selectively attachable to the distal end of bar 38 when bar 38 is advanced through fistulous tract 34. Cap 50 includes a protective groove 52 for receiving a distal end of cutting blade 44 therein. Once cutting tool 40 is inserted through tissue 35 surrounding the fistula by moving cutting tool in a direction indicated by arrow 51, the distal end of cutting blade 44 is inserted into groove 52 and held therein. The entire device, including bar 38 and cutting tool 40 is rotated as indicated by arrow 53 to core the fistulous tract from the surrounding tissue. During this rotation, cutting edge 48 of cutting blade 44 incises the tissue surrounding fistulous tract 34 while the distal end of cutting blade 44 is retained in groove 52, thereby excising fistula 32 from the surrounding tissue so that it can then be removed from the patient.

Figure 2:
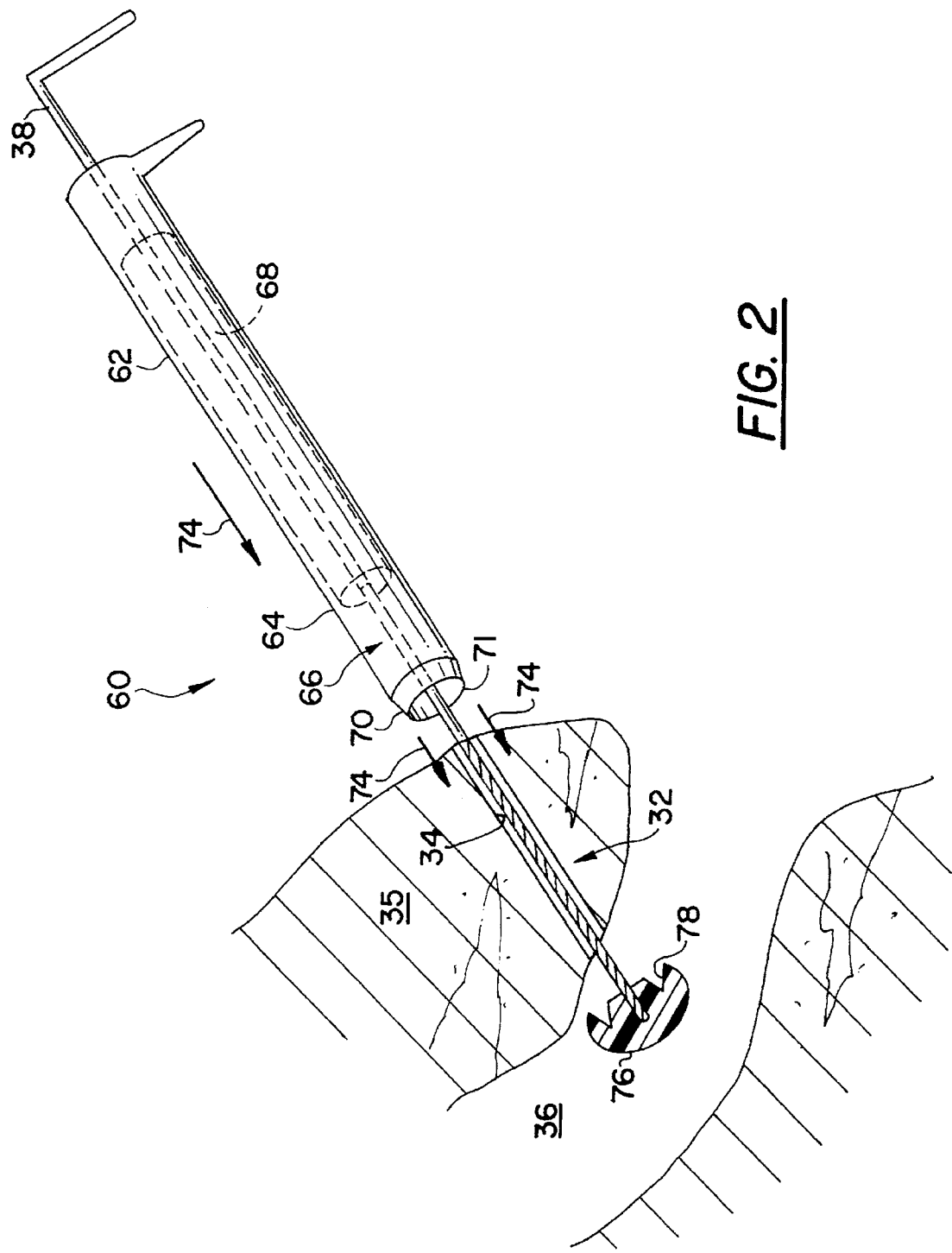
FIG. 2 is a side view, partially in section, of a second embodiment of a device and method for excising a fistula according to the principles of the present invention.

FIG. 2 illustrates a second embodiment of a device, generally indicated at 60, for removing a fistula 32. As in the first embodiment, device 60 includes bar 38. Device 60 includes a cutting tool 62 having a cylinder body portion 64 which slides in a direction generally parallel to the longitudinal axis of bar 38. As in the previous embodiment a cylindrical-shaped stabilizer 68 is fixed to bar 38 so that a space 66 is maintained between a cutting blade 70 and bar 38. In the illustrated embodiment, cutting blade 70, which is attached to the distal end of body portion 64, is circular and corresponds generally to the shape of cylindrical body portion 64.

Fistula 32 is removed using device 60 in a manner similar to that discussed above with respect to the first embodiment. More specifically, cutting tool 62 is advanced through tissue 35 surrounding fistulous tract 34 by sliding cutting tool 62 in a direction indicated by arrows 74. Cutting blade 70 has a cutting edge 71 at a distal end thereof that separates tissue 35 from fistulous tract 34, thereby coring fistulous tract 34 from the surrounding tissue. Because a space 66 is defined between bar 38 and cutting blade 70 by stabilizer 68, the cored out fistulous tract enters the hollow center of body portion 64 during the coring process. Thus, in this embodiment, fistulous tract 34 remains inside cylindrical body portion 64 as it is being cored from surrounding tissue 35. In addition, this embodiment of the present invention does not require that device 60 be rotated significantly in order to core out the fistulous tract.

A selectively attachable cap 76 is provided at the distal end of bar 38. Cap 76 includes a groove 78 corresponding to cutting edge 71 for receiving cutting edge 71 of cutting blade 70 therein once the dissection of the fistulous tract is complete.

Figure 3:
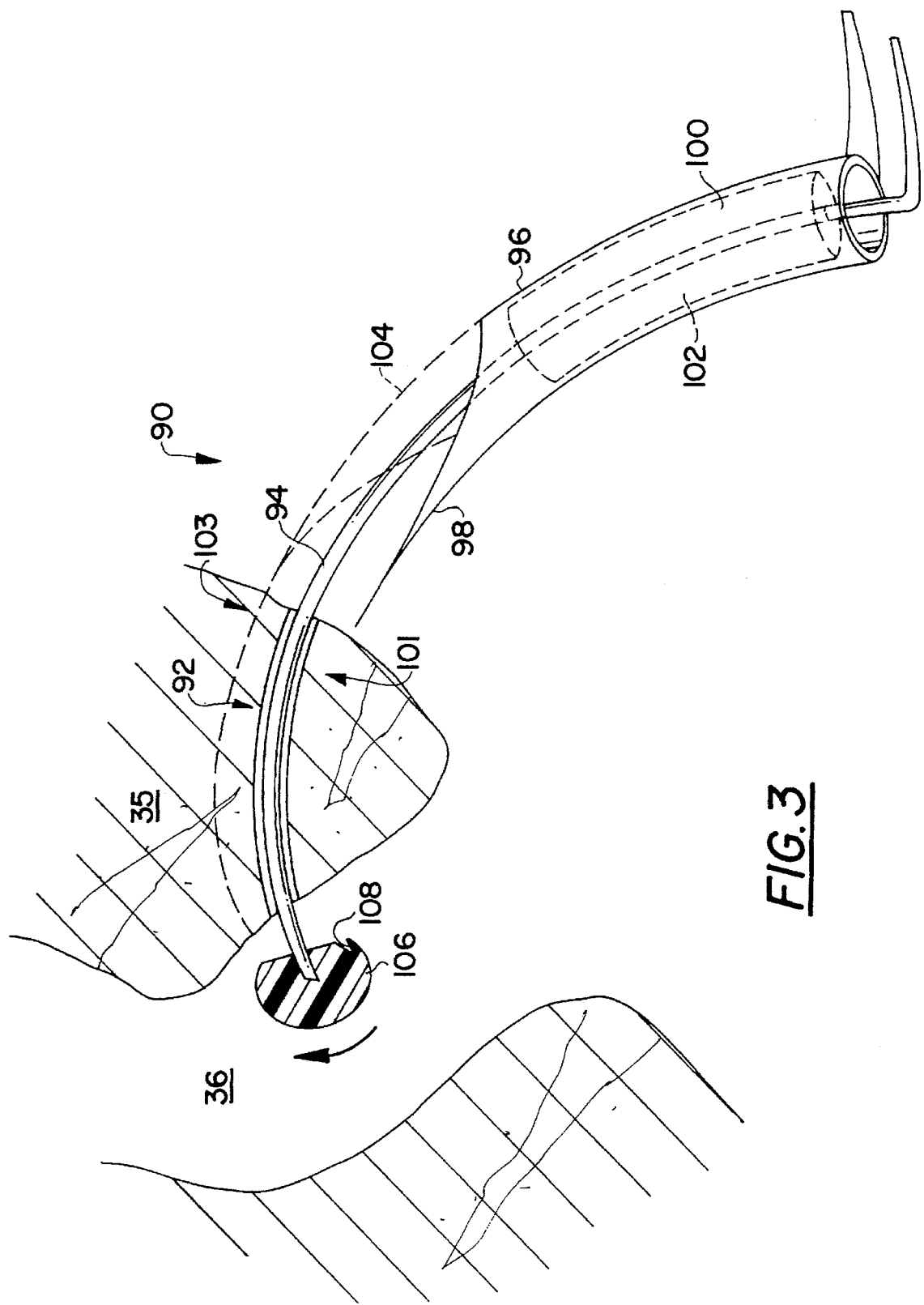
FIG. 3 is a side view, partially in section, of a third embodiment of a device and method for excising a fistula according to the principles of the present invention.

FIG. 3 illustrates a third embodiment of a device, generally indicated at 90, for excising a fistula according to the principles of the present invention. Device 90 includes a curved bar 94, which is inserted into a curved fistulous tract 92, and a curved cutting tool 96. Curved cutting blades, such as cutting blade 98 illustrated in FIG. 3, are selectively attachable to the distal end of a body portion 100 of cutting tool.

As in the previous embodiments, device 90 includes a stabilizer 102 attached to bar 94 for maintaining a space between curved bar 94 and cutting tool 96 during the fistula removal process.

Figure 4:
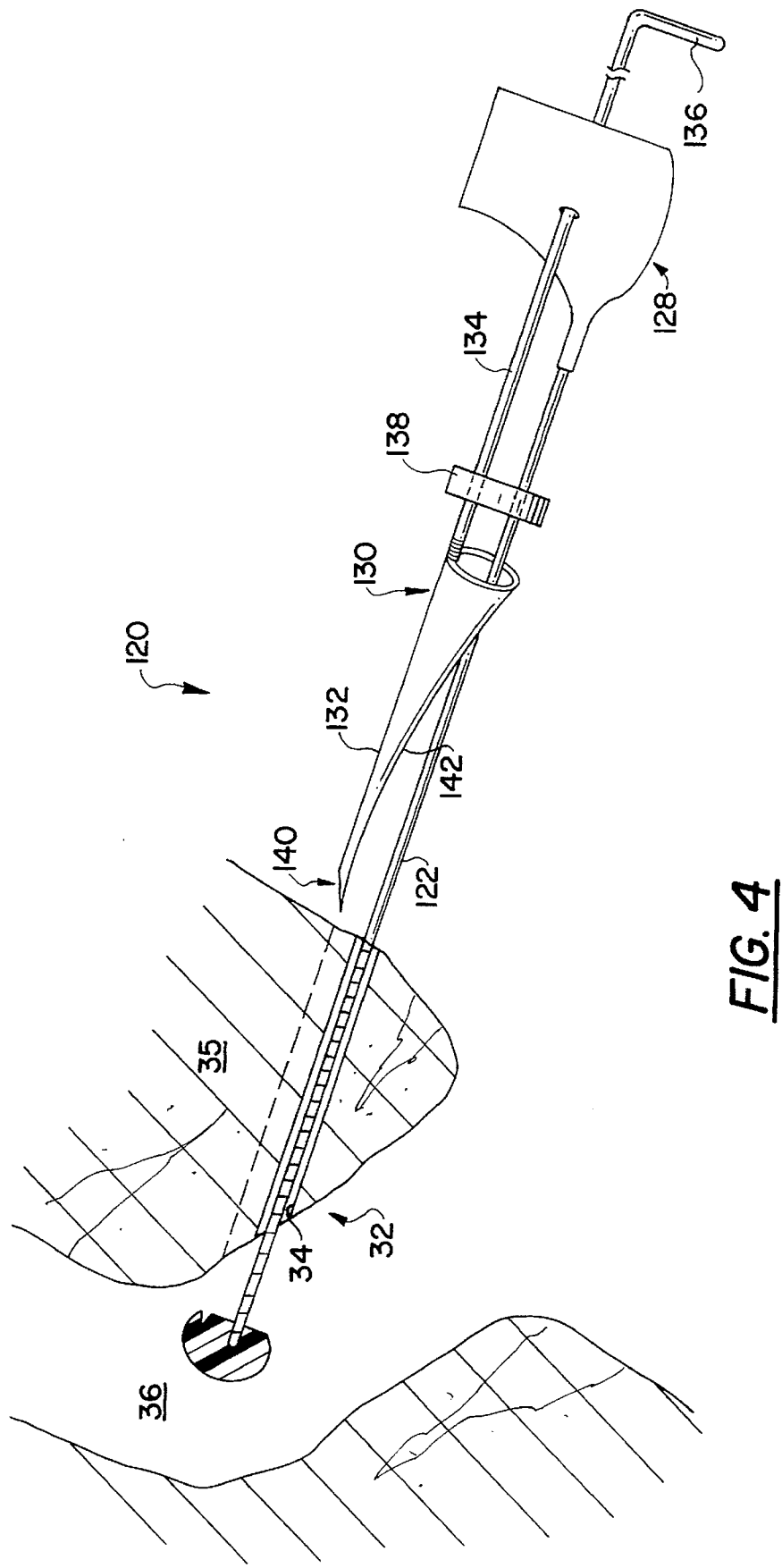
FIG. 4 is a side view, partially in section, of a fourth embodiment of a device and method for excising a fistula according to the principles of the present invention.

Because of the curvature of fistulous tract 92, at least two blades are needed to dissect fistulous tract 92 from surrounding tissue 35. In the illustrated embodiment, cutting blade 98 cuts around the inferior side 101 of fistulous tract 92 by inserting blade 98 and rotating device 90 as discussed above with respect to the first embodiment. After one side of the fistulous tract has been separated from the surrounding tissue, the first cutting blade, for example cutting blade 98, is detached from body portion 100 and a second cutting blade, for example cutting blade 104 shown by dashed lines in FIG. 4, is attached to body portion 100. Cutting blade 104 has a configuration that is substantially the same as cutting blade 98, except that cutting blade 104 is specifically curved for cutting the superior side 103 of fistulous tract 92 by inserting blade 104 and rotating device 90 as discussed above with respect to the first embodiment.

As in the first embodiment, a cap 106 is selectively attachable to the distal end of the bar. Cap 106 includes at least one groove 108 for receiving a distal end of each of the cutting blades as each is used to dissect a respective side of fistulous tract 92 from tissue 35.

FIG. 4 illustrates a fourth embodiment of a device, generally indicated at 120 for removing a fistula according to the principles of the present invention. Device 120 includes a bar 122, which is substantially similar to the bar used in the first and second embodiments discussed above. Bar 122 is inserted into the fistulous tract 34 of a fistula 32. Unlike the previous embodiments, bar 122 includes a base portion 128 attached to the proximal end thereof. A cutting tool 130 cooperates with bar 122 so that cutting tool 130 slides in a direction generally parallel to a longitudinal axis of bar 122.

Cutting tool 130 includes a cutting blade 132 selectively attachable to a body portion 134. Body portion 134 is slidably and rotatably inserted through base portion 128. A handle 136 is provided at a proximal end of body portion 134 and cutting blade 132 is attached to a distal end thereof. A stabilizer 138 is provided for maintaining a predetermined distance between cutting tool 130 during insertion and rotation of cutting blade 132 about fistulous tract 34.

In the illustrated embodiment, cutting blade 132 has a sharp end 140 and tapers in a direction toward sharp end 140 to facilitate penetration of cutting blade 132 into tissue 35 surrounding fistulous tract 34. Edges 142 of cutting blade 132 can also be sharpened so that dissection of fistulous tract 134 from surrounding tissue 3S can be accomplished by rotating cutting blade 132 about the fistulous tract.

The method of using device 120 to remove fistula 32 is the same at that discussed above with respect to the first embodiment of the present invention. Therefore, a detailed discussion of the method for removing a fistula using the device illustrated in FIG. 4 is omitted.

The joint attachment between bar 122 and cutting tool 130 at base 128 and stabilizer 138 provides a more stable operation of device 120 without requiring a large mass for the body portion.

Figure 5:
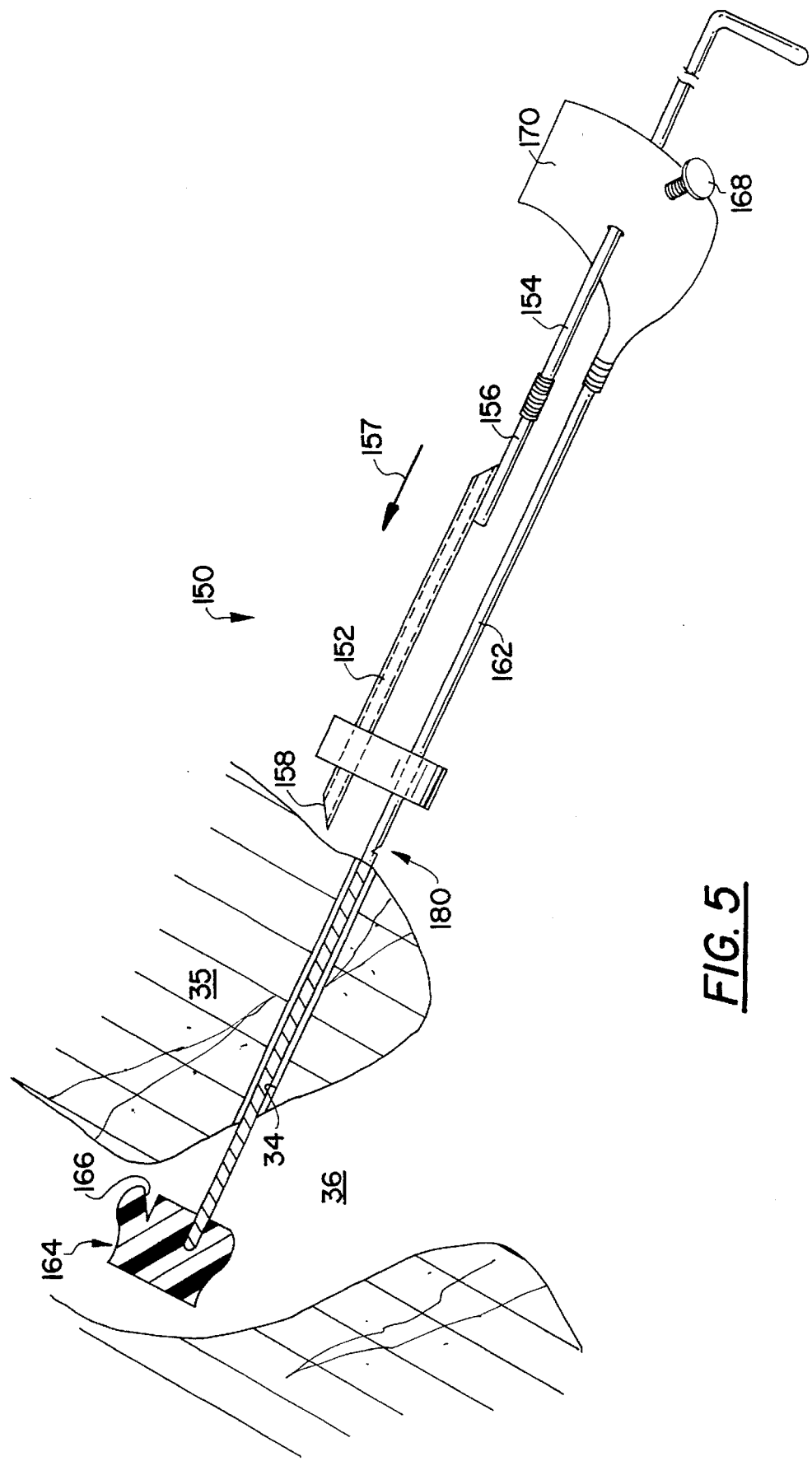
FIG. 5 is a side view, partially in section, of a fifth embodiment of a device and method for excising a fistula according to the principles of the present invention.
Figure 6:
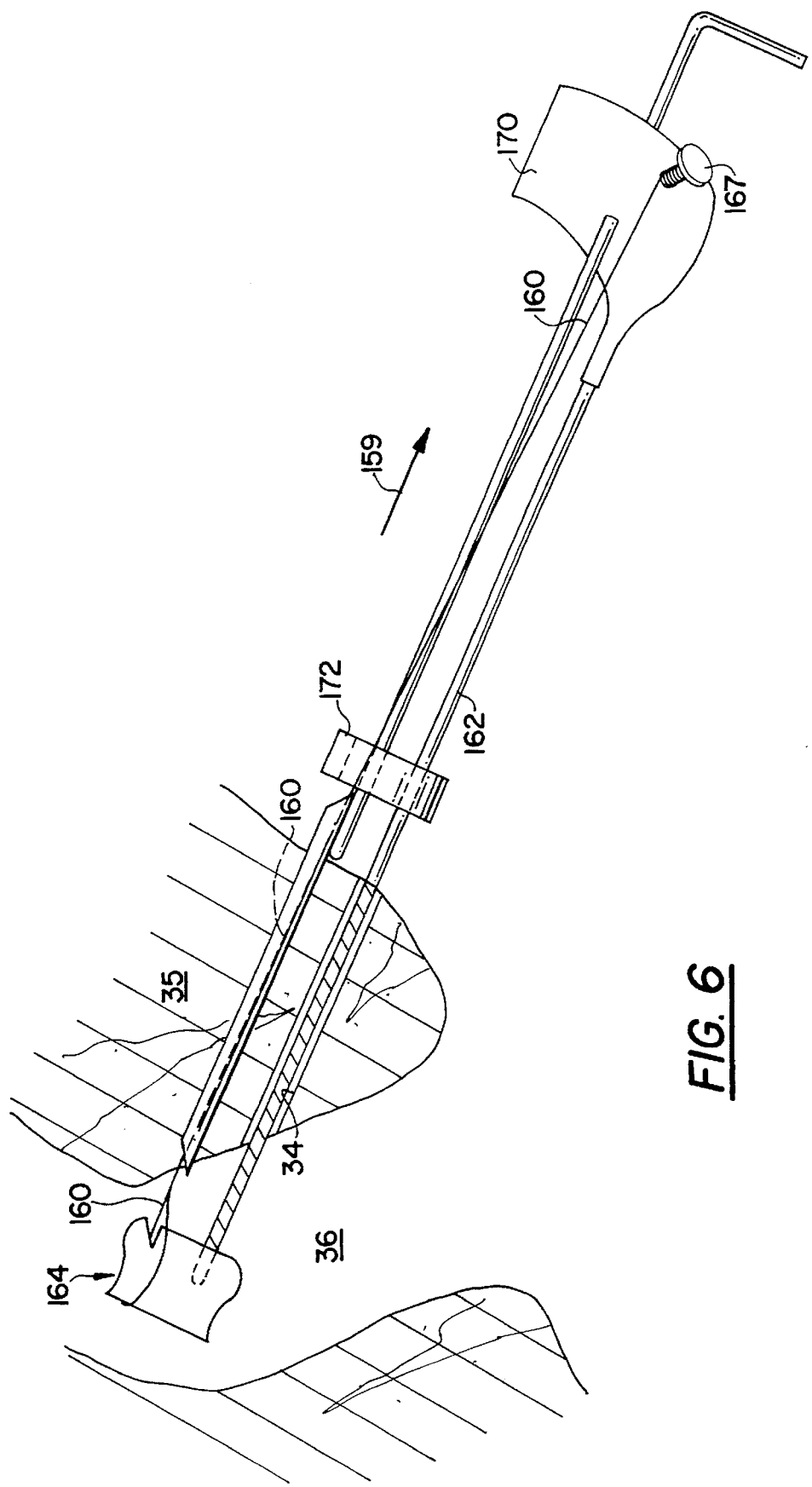
FIG. 6 is a side view, partially in section, showing the operation of the device illustrated in FIG. 5.

FIGS. 5 and 6 illustrate a fifth embodiment of a device, generally indicated at 150 for removing a fistulous tract 34 from surrounding tissue 35. In this embodiment, the cutting blade of the previous embodiments is replaced with a wide bore needle 152 attached to a body portion 154 of cutting tool 156.

Needle 152 has a cutting edge 158 that penetrates tissue 35 surrounding fistulous tract 34 by moving cutting tool 156 in a direction generally indicated by arrow 157. Once cutting edge 158 exits from tissue 35 surrounding fistulous tract 34 in anal canal 36, a strong wire 160 is threaded through needle 152 and attached to the distal end of a bar 162. In the illustrated embodiment, wire 160 is attached to a cap 164 which is attached to the distal end of bar 162. A groove 166 is provided in cap 164 for assisting in attachment of wire 160 to cap 164. It is to be understood, however, that the present invention contemplates any means for attaching wire 160 to the distal end of bar 162.

Needle 152 is then withdrawn by moving cutting tool 156 in a direction indicated by arrow 159 and wire 160 is stretched by screw 168, which is either coupled to a base portion 170 or bar 162. In the illustrated embodiment, wire 160 is wrapped around screw 168 so that rotating screw 168 causes wire 160 to become taunt and to extend in a direction generally parallel to the longitudinal axis of bar 162.

A stabilizer 172 is provided to ensure that wire 160 remains parallel with bar 162.

Rotating cutting tool 156 about fistulous tract 34 causes wire 160 to dissect the fistulous tract from the surrounding tissue. It is to be understood that wire 160 may be a cauterizing wire, so that the tissue is cauterized as it is being dissected.

In the illustrated embodiment, a groove 180 is provided in bar 162 so that fistulous tract 34 can be tied to bar 180 after it is initially cored from the surrounding tissue. This serves to stabilize fistulous tract 34 and maintain it in a stretched position as it is cored from the surrounding tissue.

Figure 7:
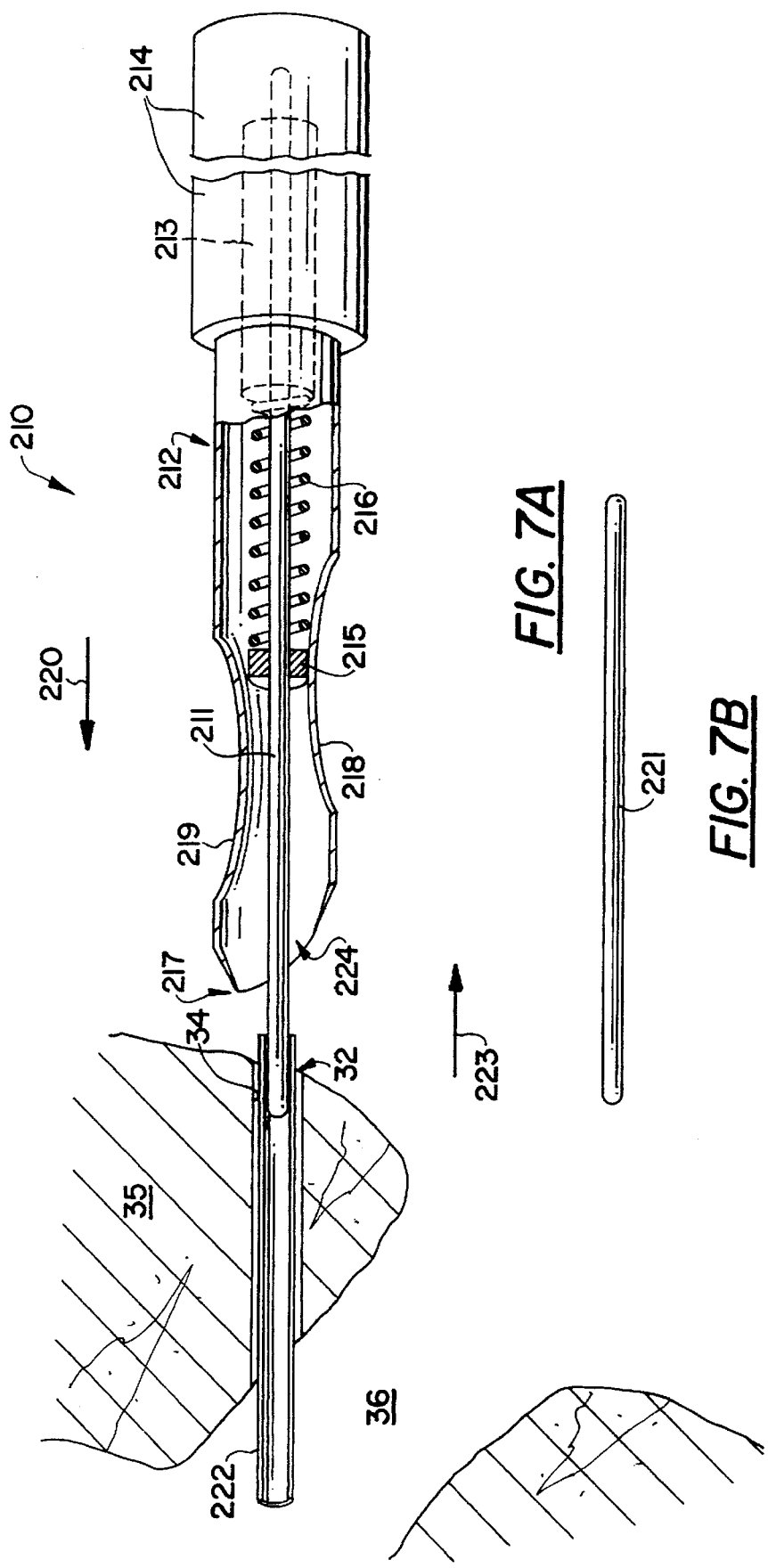
FIG. 7 is a side view, partially in section, showing a sixth embodiment of a device and method for excising a fistula according to the principles of the present invention.

FIG. 7 illustrates a sixth embodiment of a device, generally indicated at 210, for removing a fistula according to the principles of the present invention. Device 210 includes a thin bar 211 which is fixed along the longitudinal axis of a generally cylindrical shaped cutting tool 212 by fixing both to a common base 213. Common base 213, in turn, is fixed within a body 214 which is adapted to be manually gripped by a surgeon. Thin bar 211 is maintained in parallel with respect to the walls of cutting tool 212 by a disk-like stabilizer piece 215 which is slidable on bar 211 and located within cutting tool 212. The position of disk-like piece 215 is maintained initially near the tip of the cutting tool by a spring 216.

Cutting tool 212 has a selectively detachable cutting blade 217 located at the distal end thereof. The body of cutting tool 212 is provided with grooves 218 and 219 to minimize friction between the surrounding tissue 3B and the cutting tool.

The process for removing a fistula using the device of this embodiment is discussed below. The distal end of bar 211 is inserted into fistula 32 to act as a splint. Then the device 210 is thrust along the course of fistulous tract 34 as indicated by arrow 220 to thereby remove the fistulous tract.

To minimize the possibility of bar 211 penetrating the walls of fistulous tract during the manipulation of device 210, an accessory thin bar 221, which has the same caliber of bar 211, is first introduced into fistulous tract 34. Because accessory bar 221 is not associated with other components it can be more easily manipulated and properly inserted into fistulous tract 34. A sheath 222, which is made from a material suitable for insertion into a human body, such as a surgical metal, is then inserted over accessory bar 221 and slide along bar 221 until sheath 222 reaches the anal canal 36. The accessory bar 221 is then withdrawn from the fistulous tract 34 leaving only sheath 222 within the fistula. The fistulous tract can then be removed by inserting bar 211 into sheath 222 and using sheath 222 as a guide for cutting tool 212 so that cutting tool 212 is not displaced from the fistulous tract during the removal process.

The excised fistulous track enters lumen 224 of cutting tool 212 and pushes the disk-shaped stabilizer 215 against the force provided by spring 216, thus creating a space to accommodate the entire length of the excised fistulous tract.

The cutting edge of the cutting tool can be insulated and connected to a cauterizing diathermy to assist in the excision of the fistulous tract and coagulation of the surrounding tissue.

Figure 8:
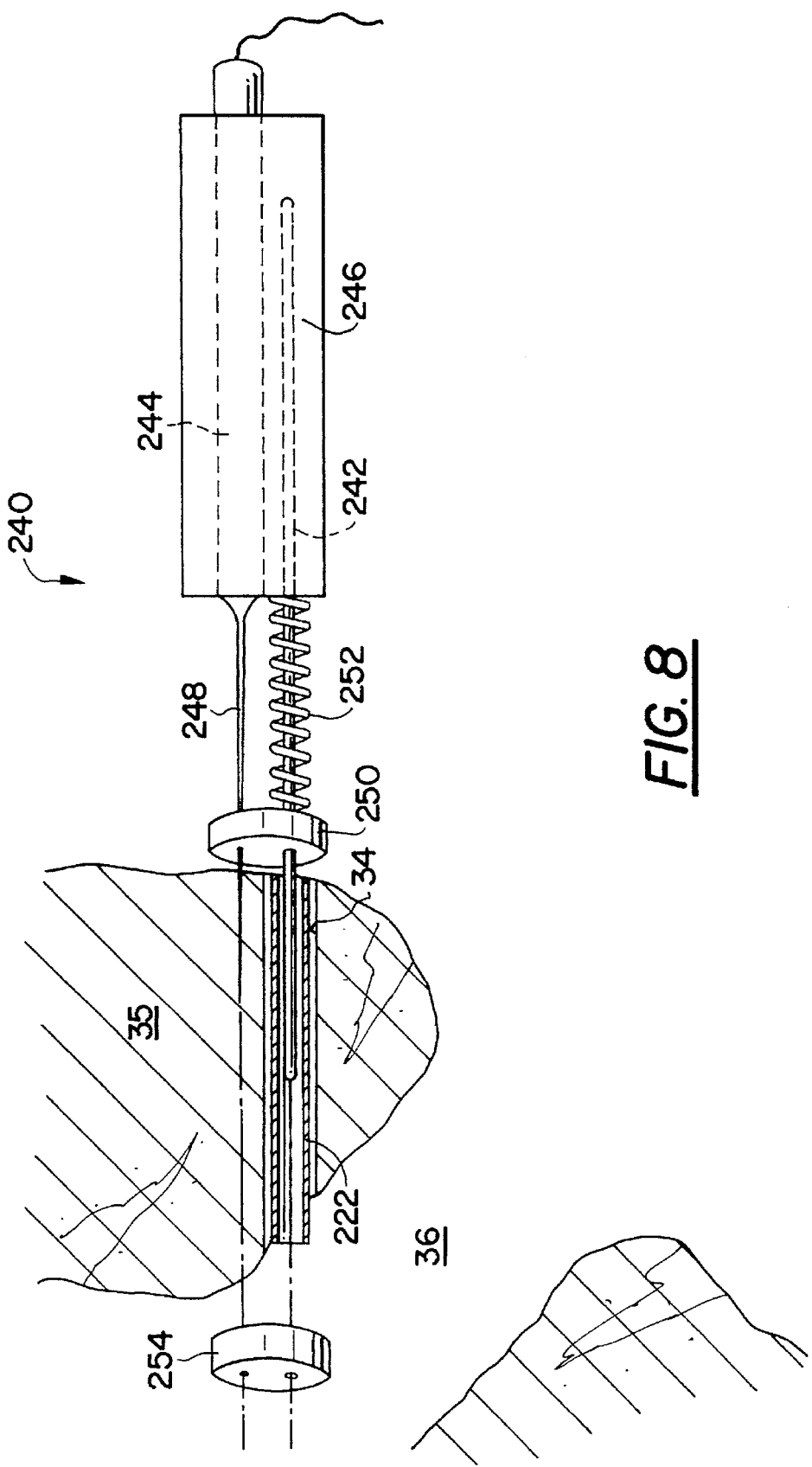
FIG. 8 is a side view, partially in section, showing a seventh embodiment of a device and method for excising a fistula according to the principles of the present invention.

FIG. 8 illustrates a seventh embodiment of a device, generally indicated at 240, for removing a fistula according to the principles of the present invention. Device 240 is similar in operation to the device illustrated in FIGS. 5 and 6, except that a diathermy needle 248 is used as a cutting tool to remove the fistulous tract 34 from surrounding tissue 35. A diathermy needle is beneficial in that it provides both a cutting and coagulating function. Device 240 includes a thin bar 242 coupled to diathermy handle 244, by a coupling piece 246 or base so that diathermy needle 248 and thin bar 242 are maintained parallel to one another. A stabilizer 250 is provided to further maintain diathermy needle 248 parallel to thin bar 242. A spring 252 is provided between coupling piece 246 and stabilizer 250 surrounding thin bar 242 to maintain stabilizer 250 near the distal end of diathermy needle 248 until diathermy needle 248 is inserted.

A second stabilizer 254 is provided within anal canal 36, for example, so that the distal ends of thin bar 242 and diathermy needle 248 can be inserted into openings provided in second stabilizer 252 after insertion of diathermy needle 248 through surrounding tissue 35 is complete. Fistulous tract 34 is removed (cored out) by energizing diathermy needle 248 and rotating the charged diathermy needle about fistulous tract 34. The method by which thin bar 242 is inserted into fistulous tract 34 is similar to that discussed above with respect to FIG. 7. That is, a sheath 222 is first inserted into fistulous tract 34 using an accessory bar (not shown). Thin bar 242 is then inserted into the hollow center of sheath 222 for easily positioning device 240 relative to the fistulous tract to be removed.

Figure 9:
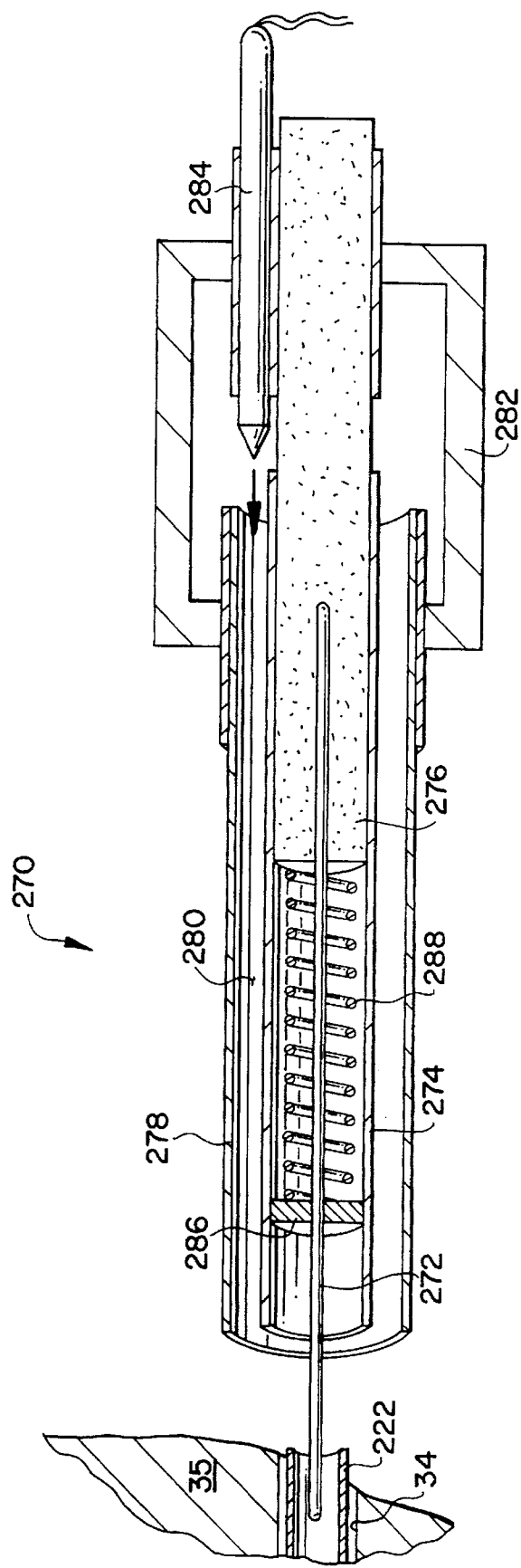
FIG. 9 is a side view, partially in section, showing a eight embodiment of a device and method for excising a fistula according to the principles of the present invention.

FIG. 9 illustrates an eighth embodiment of a device, generally indicated at 270, for removing a fistula according to the principles of the present invention. In this embodiment, a laser beam type cutting device 284 is used to separate fistulous tract 34 from surrounding tissue 35. A laser type cutting device, like the diathermy needle, provides both a cutting and coagulating function.

Device 270 includes a thin bar 272 coaxially located within a first cylinder 274. A proximate end of thin bar 272 and a proximate end of first cylinder 274 are attached to one another via a holding piece 276 so that thin bar 272 is maintained in parallel with respect to cylinder 274. A second, larger diameter, cylinder 278 is located outside cylinder 274 and coaxially aligned therewith so as to define a space 280 of approximately 2 mm between first cylinder 274 and second cylinder 278. A coupling device 282 maintains the coaxial alignment between first cylinder 274 and second cylinder 278 so that a laser beam emitted from laser emitting device 284 travels in space 280 defined between first cylinder 274 and second cylinder 278. Coupling device 282 also allows a laser emitting device 284 to be rotated so that the laser beam is rotated along space 280 about an outer circumference of first cylinder 274 and an inner circumference of second cylinder 278. A disk-like stabilizer piece 286 is provided inside first cylinder 274 and is slidable over thin bar 272. Stabilizer piece 286 serves to maintain the parallel spaced relationship between thin bar 272 and first cylinder 274. A spring 288 maintains stabilizer piece 286 near the distal end of first cylinder 274.

The operation of device 270 is discussed below. First, a sheath 222 is inserted into the fistulous tract 34, as discussed above with respect to FIGS. 7 and 8. Thin bar 272 is then inserted into the hollow sheath so that the distal ends of the first and second cylinders 274 and 278 are adjacent to and surround the fistulous tract. The laser emitting device is energized and rotated about a longitudinal axis of said bar so as to dissect fistulous tract 34 from surrounding tissue 35. Device 270 is advanced along the fistulous tract as the cutting process continues. The dissected fistulous tract enters first cylinder 274 forcing stabilizer 286 toward coupling device 282. The second cylinder 278 retracts the surrounding tissue from the ablation area so that the entire fistulous tract can be cored out from the surrounding tissue. It is to be understood that the laser emitting device can be rotated manually or motor driven. Furthermore, computers can be used to the control the operation of the laser emitting device.

It is to be understood that the devices for removing a fistula and the individual components of these devices can have a wide variety of different designs, shapes and sizes. In addition, it may be made up of a number of different parts and different materials. For example, a cylindrical sheath can be mounted on the thin bar to stretch and splint the fistulous tract if the fistulous tract is too wide for the standard size of the bar. In addition, the device can have a telescopic design where the bar acts as a probe and inner sheaths are fixed to the bar and protrude for a few inches along the bar to provide space to accommodate the coredout fistula which is dissected by a sliding external sheath used as a cutting tool.

While the present invention has been described in conjunction with what is presently considered to be the most practical preferred embodiments, it is to be understood that the invention is not to be limited to the disclosed embodiments, but on the contrary, is intended to cover various modifications and equivalent arrangements included within the spirit and scope of the appended claims.

What is claimed is:

1. A device for excision of a fistula, which includes a fistulous tract, said device comprising:

a first bar having a longitudinal axis and adapted to be inserted into the fistulous tract;

a cutting tool cooperating with said first bar;

a common base fixing a proximal end of said first bar to a proximal end of said cutting tool so that said first bar does not move relative to said cutting tool and remains parallel to said cutting tool, the fistulous tract being excised by moving said device relative to the fistulous tract to thereby core the fistulous tract from surrounding tissue;

a disk-shaped stabilizer which is slidable over said first bar within a body of said cutting tool so as to maintain said first bar in parallel to said cutting tool; and a spring for maintaining said stabilizer near a distal end of said cutting tool, wherein excised portions of the fistulous tract slide between said first bar and said cutting tool and push against said stabilizer, thereby compressing said spring as said device is advanced along said fistulous tract.

2. A device as defined in claim 1, wherein said cutting tool includes a body portion and a selectively detachable cutting blade.

3. A device as defined in claim 1, wherein said first bar and said cutting tool are curved.

4. A device as defined in claim 1, further comprising a cap selectively attachable to a distal end of said first bar, said cap including a groove for receiving a distal end of said first bar therein.

5. A device as defined in claim 1, wherein said body portion has grooves in an exterior surface thereof to minimize the friction between said cutting tool and the surrounding tissue.

6. A device as defined in claim 1, wherein said body portion has a generally cylindrical shape so as to surround a portion of said bar.

7. A device as defined in claim 1, wherein said cutting tool includes a non-circular cutting edge at said distal end thereof.

8. A device as defined in claim 1, further comprising:

an accessory bar having a caliber substantially matching a caliber of said first bar; and a sheath, wherein said accessory bar is adapted to be inserted into the fistulous tract and said sheath is adapted to be inserted over said accessory bar for locating said sheath within the fistulous tract and enabling said accessory bar to be removed from within said sheath so that said sheath acts as a guide for said first bar during excision of said fistulous tract.

9. A device for excision of a fistula, which includes a fistulous tract, said device comprising:

a first bar having a longitudinal axis and adapted to be inserted into the fistulous tract;

a cutting tool cooperating with said first bar;

a common base connecting said first bar to said cutting tool so that said first bar remains parallel to said cutting tool, the fistulous tract being excised by moving said device relative to the fistulous tract to thereby core the fistulous tract from surrounding tissue;

an accessory bar having a caliber substantially matching a caliber of said first bar;

and a sheath, wherein said accessory bar is adapted to be inserted into the fistulous tract and said sheath is adapted to be inserted over said accessory bar for locating said sheath within the fistulous tract and enabling said accessory bar to be removed from within said sheath so that said sheath acts as a guide for said first bar during excision of said fistulous tract.

* * * * *

UNITED STATES PATENT AND TRADEMARK OFFICE
CERTIFICATE OF CORRECTION

PATENT NO. : 5,643,305
DATED : July 1, 1997
INVENTOR(S) : AL-TAMEEM

It is certified that error appears in the above-identified patent and that said Letters Patent is hereby corrected as shown below:

On the Title Page: item

"[76] Inventor: Moshin Al-Tameem"
        should be
--[76] Inventor: Mohsin Al-Tameem--.

Signed and Sealed this

Second Day of December,1997

Attest:

BRUCE LEHMAN

Attesting Officer        Commissioner of Patents and Trademarks